United States Patent
Koit et al.

(10) Patent No.: US 10,753,924 B2
(45) Date of Patent: Aug. 25, 2020

(54) METHOD FOR SELECTING PATIENTS RESPONSIVE FOR CANCER TREATMENTS

(71) Applicant: Mitogro OÜ, Tallinn (EE)

(72) Inventors: Andre Koit, Tallinn (EE); Tuuli Käämbre, Tallinn (EE)

(73) Assignee: Mitogro OÜ, Tallinn (EE)

( * ) Notice: Subject to any disclaimer, the term of this patent is extended or adjusted under 35 U.S.C. 154(b) by 432 days.

(21) Appl. No.: 15/651,003

(22) Filed: Jul. 17, 2017

(65) Prior Publication Data

US 2018/0017547 A1 Jan. 18, 2018

Related U.S. Application Data

(60) Provisional application No. 62/363,314, filed on Jul. 17, 2016.

(51) Int. Cl.
G01N 33/50 (2006.01)
G01N 33/574 (2006.01)

(52) U.S. Cl.
CPC ..... *G01N 33/5038* (2013.01); *G01N 33/5079* (2013.01); *G01N 33/5091* (2013.01); *G01N 33/57496* (2013.01); *G01N 33/57415* (2013.01); *G01N 33/57419* (2013.01); *G01N 2800/52* (2013.01); *G01N 2800/7028* (2013.01); *G01N 2800/7076* (2013.01)

(58) Field of Classification Search
CPC ......... G01N 33/5038; G01N 33/57496; G01N 33/5079; G01N 33/5091; G01N 2800/52; G01N 2800/7028; G01N 2800/7076
See application file for complete search history.

(56) References Cited

U.S. PATENT DOCUMENTS

2002/0127619 A1 9/2002 Jett et al.
2016/0320316 A1 11/2016 Pothier et al.

OTHER PUBLICATIONS

Nicolae et al. (Metabolic Engineering, 2015, 32:95-105) (Year: 2015).*
Petrarulo M. et al. "Citrate in Urine Determined with a New Citrate Lyase Method", Clin. Chem. 41/10, 1995, pp. 1518-1521.

* cited by examiner

*Primary Examiner* — Jeremy C Flinders
(74) *Attorney, Agent, or Firm* — Laine IP Oy (57) ABSTRACT

The present invention is directed to a method of quantifying intracellular metabolite effluxes in permeabilized cancer cells for selecting cancer patients responsive for a cancer treatment, the method comprising the steps of: a) providing a sample of cancer cells taken from a patient; b) permeabilizing said cancer cells; c) incubating said permeabilized cancer cells in a reaction medium for a period of time allowing biological activity of intracellular organelles and accumulation of metabolites produced by said activity into the reaction medium in the presence of a substrate or substrates relating to a metabolite efflux or effluxes of interest, wherein said substrates used are at least glutamine and pyruvate; d) determining the quantity of metabolites relating to said metabolite efflux or effluxes of interest accumulated in the reaction medium during step c); and e) comparing the amounts of metabolites determined in step d) to equal measurements performed on control samples of the same tissue type and assessing the aggressiveness of the cancer cells or the treatment response of the cancer cells to a drug affecting a metabolic pathway or pathways relating to said metabolite efflux or effluxes of interest.

16 Claims, 5 Drawing Sheets

| Subtypes | Substrates | | | count | count% |
|---|---|---|---|---|---|
| | Glutamate | Pyruvate | Pal.Car. | | |
| Luminal A | 93 | 134 | 124 | 21 | 36% |
| Luminal B | 93 | 138 | 143 | 19 | 32% |
| HER2+ | 117 | | | 6 | 10% |
| TripNeg | 128 | | 135 | 10 | 17% |
| LumB/HER2+ | | | | 3 | 5% |
| | | | | 59 | 100% |

| Grade | Substrates | | | count | count% |
|---|---|---|---|---|---|
| | Glutamate | Pyruvate | Pal.Car. | | |
| 1 | 90 | | | 15 | 25% |
| 2 | 105 | | | 26 | 44% |
| 3 | 116 | | | 18 | 31% |
| | | | | 59 | 100% |

| Ki-67 | Substrates | | | count | count% |
|---|---|---|---|---|---|
| | Glutamate | Pyruvate | Pal.Car. | | |
| <14 | 97 | 129 | | 22 | 37% |
| >14 | 108 | | | 37 | 63% |
| | | | | 59 | 100% |

| Diameter | Substrates | | | count | count% |
|---|---|---|---|---|---|
| | Glutamate | Pyruvate | Pal.Car. | | |
| <2 cm | 89 | | | 22 | 37% |
| >2 cm | 117 | | | 37 | 63% |
| | | | | 59 | 100% |

METHOD FOR SELECTING PATIENTS RESPONSIVE FOR CANCER TREATMENTS

FIELD OF THE INVENTION

The present invention relates to cancer diagnostics and therapies and in particular to the detection of metabolic alterations in cancer cells that are diagnostic, prognostic and/or predictive and which can be used for selecting patients suffering from cancer that are responsive to treatment with a drug affecting mitochondrial metabolism.

BACKGROUND OF THE INVENTION

Assessing aggressiveness of a given tumor sample can help physicians advise between aggressive treatment and active surveillance of the disease (e.g. in case of early stage breast cancer and prostate cancer). In such way only patients with aggressive disease get active treatment and patients with least aggressive disease can settle with active surveillance just to be sure that their disease does not progress (in such case chemotherapy, surgery, radiotherapy or other treatment, like hormone- or immunotherapy, is not applied leading to social and economic benefits).

Attempts have been made with methods for categorizing cancers based on the aggressiveness. For instance, US20160320316 discloses a method for determining, in vitro, aggressiveness grade of cancer cells originating from solid tissue suspected of being cancerous, wherein the categorizing is based on the electromagnetic signature of the cells. In US20020127619 a method of diagnosing stage or aggressiveness of breast and prostate cancer based on levels of fatty acid binding proteins is disclosed. Neither of the named methods have been taken into routine use by clinics. In standard clinical setting, immunohistochemistry has been widely used, but studies have shown significant discordance between results from different labs and even between different pathologists within a same lab. Therefore, predicting tumor aggressiveness has remained difficult and controversial.

In the present invention, time-dependent intracellular metabolite fluxes in the cytosol of cancer cells were studied. Differences in metabolite fluxes in samples of the same type (e.g. tumor samples) supported predictions for assessing metabolic activity (e.g. aggressiveness) of a given sample (e.g. expected need for aggressive therapy or active surveillance) or predicting response to treatment with drugs targeting pathways or enzymes contributing to fluxes that can be quantified using the method described below.

Oncological drugs often have low response rates due to intrinsic peculiarities between or within tumors that often cannot be predicted with standard methods. That is particularly true for drugs targeting mitochondrial metabolism in tumors. In case of mutant IDH (iso-citrate dehydrogenase) 1 and mutant IDH 2 the response rate in treated patients is up to 40%; in case of glutaminase inhibitors the response rate is lower. Treatment against mutant IDH is applied only among patients with the said mutation, but response rate in such setting is still as low as mentioned. For glutaminase inhibitors no confirmed biomarkers have been found to stratify patients and to increase response rate among treated patients. In such situation, the method described herein could be a valuable tool to stratify patients as the metabolic pathways that these drugs, among others, are affecting, can be directly measured and quantified in tumor samples prior to assigning them to treatment groups. Both surgical samples or biopsies can be used for the method described here.

SUMMARY OF THE INVENTION

In the present invention, it is surprisingly discovered that it is possible to quantify intracellular mitochondrial metabolite efflux rates in permeabilized cancer cells in time dependent manner so that metabolic dependencies and the level of aggressiveness of the cancer cells in a sample can be detected. The metabolic dependencies, based on the present invention, are also used for selecting cancer patients predicted to be responsive for a cancer treatment, the method comprising the steps of:
a) providing a sample of cancer cells taken from a patient;
b) permeabilizing said cancer cells;
c) incubating said permeabilized cancer cells in a reaction medium for a period of time allowing biological activity of intracellular organelles and accumulation of metabolites produced by said activity into the reaction medium in the presence of a substrate or substrates relating to a metabolite efflux or effluxes of interest, wherein the substrates used are at least glutamine and pyruvate;
d) determining the quantity of metabolites relating to said metabolite efflux or effluxes of interest accumulated in the reaction medium during step c);
e) comparing the amounts of metabolites determined in step d) to equal measurements performed on control samples of the same tissue type and assessing the aggressiveness of the cancer cells or the treatment response of the cancer cells to a drug affecting a metabolic pathway or pathways relating to said metabolite efflux or effluxes of interest.

DETAILED DESCRIPTION OF THE INVENTION

The term "tumor," as used herein, refers to any neoplastic cell growth and proliferation, whether malignant or benign, and all pre-cancerous and cancerous cells and tissues.

The terms "cancer" and "cancerous" refer to or describe the physiological condition in mammals that is typically characterized in part by unregulated cell growth. Examples of cancer include, but are not limited to, colorectal cancer, breast cancer, ovarian cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, myeloblastic syndrome, multiple myeloma, acute myelogenous leukemia, chronic myelogenous leukemia, acute lymphocytic leukemia, chronic lymphocytic leukemia, lymphoma, rectal cancer, and esophageal cancer. In an exemplary embodiment, the cancer is preferably breast cancer.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease, such as cancer, or symptom thereof and/or may be therapeutic in terms of effecting a partial or complete cure for a disease and/or symptoms of the disease. "Treatment," as used herein, covers any treatment of a disease, such as cancer, in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease); (b) inhibiting the disease, i.e., arresting its development; and (c) relieving the disease, i.e., causing regression or halting progression of the disease.

As used herein in the context of patient response to a cancer treatment, the terms "responsive", "beneficial response," "beneficial patient response," and "clinically beneficial response," "clinical benefit," and the like, are used interchangeably and refer to favorable patient response to a drug as opposed to unfavorable responses, i.e. adverse events. In individual patients, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/ or cancer cell number and/or tumor metastasis is indicative of lack of beneficial response to treatment.

In a population the clinical benefit of a drug, i.e. its efficacy can be evaluated on the basis of one or more endpoints. For example, analysis of overall response rate (ORR) classifies as responders those patients who experience CR or PR after treatment with drug. Analysis of disease control (DC) classifies as responders those patients who experience CR, PR or SD after treatment with drug.

As used herein, the term "responsive" refers to a patient who has a cancer which is dependent on a certain mitochondrial metabolic pathway, and who exhibits a beneficial clinical response following treatment with an inhibitor of said metabolic pathway.

As used herein, the term "non-responsive" refers to a patient who has a cancer which is not dependent on any certain mitochondrial metabolic pathway or presents with elevated pathways known to drive resistance and who does not exhibit a beneficial clinical response following treatment with an inhibitor of mitochondrial metabolic pathways.

The term "tumor sample" or "a sample of cancer cell" as used herein means a sample comprising tumor material obtained from a cancerous patient. The term encompasses clinical samples, for example tissue obtained by surgical resection, by collecting a blood sample, and tissue obtained by biopsy, such as for example a core biopsy or a fine needle biopsy. The term also encompasses samples comprising tumor cells obtained from sites other than the primary tumor, e.g., circulating tumor cells. The term encompasses cells that are the progeny of the patient's tumor cells, e.g. cell culture samples derived from primary tumor cells or circulating tumor cells. The term encompasses samples that may comprise protein or nucleic acid material shed from tumor cells in vivo, e.g. bone marrow, blood, plasma, serum, and the like. The term also encompasses samples that have been enriched for tumor cells or otherwise manipulated after their procurement and samples comprising polynucleotides and/ or polypeptides that are obtained from a patient's tumor material.

Figure 1:
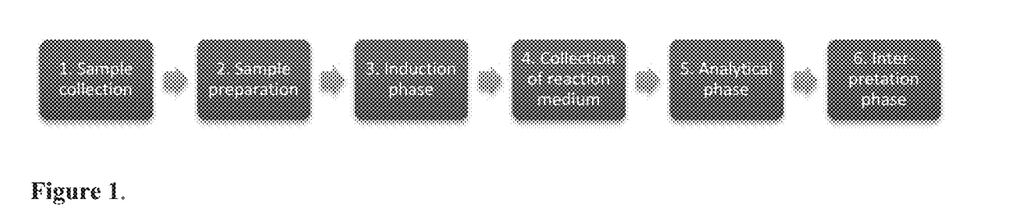
FIG. 1. Steps in the method to quantify metabolic fluxes in permeabilized cells or fibers in time dependent manner.
Figure 2:
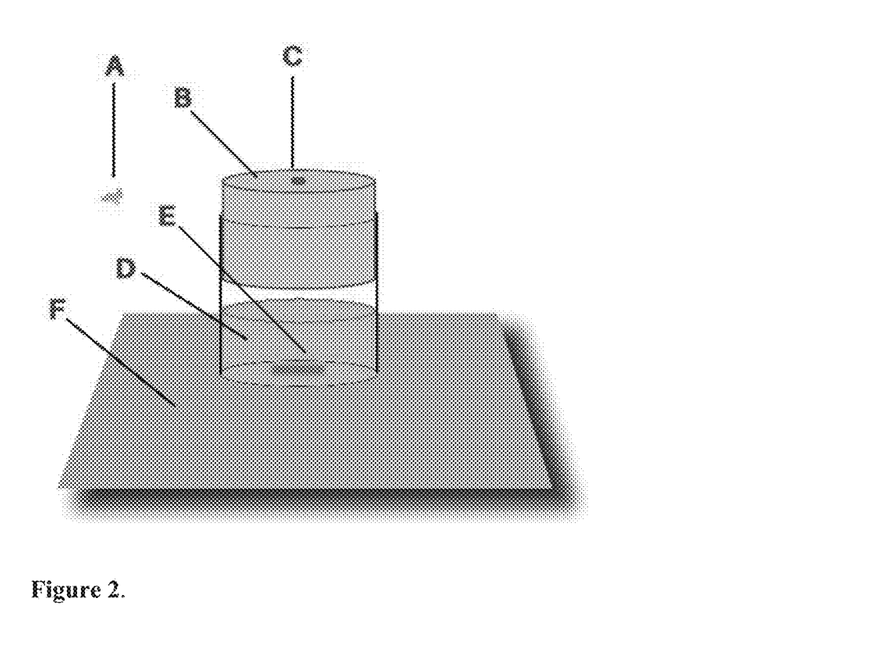
FIG. 2. General depiction of the components of the test system. A—skinned fiber or cells that are introduced to the reaction medium D; B—stopper for isolating reaction medium and sample from ambient environment; C—canal inside the stopper B for escaping air during sealing, for injecting new compounds to the reaction medium or for collecting samples during the reaction; D—reaction medium; E—magnetic stirrer; F—heating and stirring device (depicted as flat, but can also surround the reaction medium to improve temperature control).

To better understand intracellular processes, it is necessary to be able to quantify intracellular metabolite fluxes in the cytosol, in intracellular organelles isolated from cytosol via membranes or between cytosol and intracellular organelles having membranes. Here, we describe a method which is based on well-known permeabilization technology, but in the framework of the given invention, we have developed it further to be able to quantify metabolic fluxes in time-dependent manner between intracellular organelles (separated from the cytosolic compartment via membranes), like mitochondria, and cytosolic compartment. The present invention shows that based on the metabolite quantity, length of the induction phase and quantity of the sample, one can calculate time-dependent metabolic fluxes in a given sample (see FIG. 1 for a preferred workflow).

Accordingly, the present invention provides a method of quantifying intracellular metabolite effluxes in permeabilized cancer cells for selecting cancer patients responsive for a cancer treatment, the method comprising the steps of:
a) providing a sample of cancer cells taken from a patient;
b) permeabilizing said cancer cells;
c) incubating said permeabilized cancer cells in a reaction medium for a period of time allowing biological activity of intracellular organelles and accumulation of metabolites produced by said activity into the reaction medium in the presence of a substrate or substrates relating to a metabolite efflux or effluxes of interest, wherein the substrates used are at least glutamine and pyruvate;
d) determining the quantity or amount of metabolites relating to said metabolite efflux or effluxes of interest accumulated in the reaction medium during step c);
e) comparing the amounts of metabolites determined in step d) to equal measurements performed on control samples of the same tissue type and assessing the aggressiveness of the cancer cells or the treatment response of the cancer cells to a drug affecting a metabolic pathway or pathways relating to said metabolite efflux or effluxes of interest.

In a preferred embodiment, the cells are permeabilized in step b) by electro-permeabilization or by contacting the cells with a permeabilization agent. In an embodiment, said permeabilization agent is preferably selected from the group consisting of: saponin and digitonin. Other permeabilization agents, such as Triton-X100™, are known in the art.

In a preferred embodiment, said substrate or substrates relating to a metabolite efflux or effluxes of interest in step c) are selected from the group consisting of: pyruvate and glutamine. Further substrates relating to a metabolite efflux or effluxes of interest in step c) can be selected from the group consisting of: citrate, iso-citrate, glutamate, alpha-ketoglutarate, pyruvate, succinate, acylcarnitine, ornithine, arginine, serine, glycine, formate, proline, and malate. In step c), the cancer cells may be incubated with the substrate(s) in one sample or in parallel samples so that in the latter case each sample is run with only one of the substrates in use at each given time, e.g.:

Sample+pyruvate(+reaction medium)  1.

Sample+glutamine(+reaction medium)  2.

In the present method, also other control samples can be used, for instance, in a control sample said substrate relating to a metabolite efflux of interest in step c) can be an inhibitor of a metabolite efflux of interest. Examples of such inhibitors include 1,2,3-benzenetricarboxylic acid, which is a membrane transport inhibitor capable of stopping citrate efflux from mitochondria. Other examples of inhibitors are listed in Table 2.

In a preferred embodiment, said period of time in step c) is 0.1-180 minutes.

In step d) of the method, the quantity of metabolites relating to said metabolite efflux or effluxes of interest accumulated in the reaction medium during step c) is determined. A person skilled in the art is able to use any analytical device or method to quantify the metabolites of interest in the reaction medium. Both accumulation and decrease of the substrates and metabolites can be measured.

In a preferred embodiment, a further substrate used in step c) is an acylcarnitine, more preferably palmitoylcarnitine or octanoylcarnitine. Other metabolites which can be determined in step d) are selected from the group consisting of: citrate, alpha-ketoglutarate, folate, ATP, ADP, citrulline, ornithine, oxaloacetate, δ-aminolevulinic acid, alanine, arginine, asparagine, aspartate, cysteine, glutamate, glycine, histidine, isoleucine, leucine, lysine, methionine, proline, serine, threonine, tryptophan, phenylalanine, tyrosine, valine, $H_2O_2$, carnitine, phosphoenolpyruvate, formate, fumarate, succinate, iso-citrate, urea, and 2-hydroxy-glutarate. More preferably, the metabolites determined in step d) are citrate, alpha-ketoglutarate, and oxaloacetate.

In interpretation step e), the amounts of metabolites determined in step d) and equal measurements performed on control samples of the same tissue type, such as healthy tissue samples taken from the same patient or results from healthy or cancerous tissue samples from previous patients suffering from a similar condition, are compared to each other, and in this way the aggressiveness of the cancer cells or the treatment response of the cancer cells to a drug affecting a metabolic pathway or pathways relating to said metabolite efflux or effluxes of interest is assessed. Combining length of the induction phase, concentration of the metabolites of interest as analyzed in the analytical phase and quantity of the given sample, time-dependent fluxes can be calculated (e.g. amount of metabolite÷unit of sample× amount of time).

Time-dependent metabolite fluxes can be used to position the analyzed samples in the set of results gained from samples of equal types (e.g. within breast cancer samples, within molecular subtypes of breast cancer, within samples from patients diagnosed with acute myeloid leukemia etc.). Based on the comparison of calculated results, predictive and/or prognostic assessment can be made when the clinical outcome of the comparative dataset is known. Such prognostic assessment can be made, among others, for assessing metabolic activity (e.g. aggressiveness) of the given sample (e.g. if the disease requires aggressive treatment or if active surveillance is favored) or for predicting treatment response to drugs or biological compounds targeting pathways or relying on pathways that can be quantified and compared as result of this method. If extended reliance on quantified pathways is of interest, then exogenous enzyme, enzymes or chemicals can be introduced to the reaction medium to imitate the pathway of interest that goes beyond the present system in the sample.

In a preferred embodiment, in step e) said drug affecting a metabolic pathway is inhibiting or targeting mitochondrial metabolism. More preferably, said drug is affecting or inhibiting the mitochondrial glutamine metabolism. Most preferably, said drug is a glutaminase (GLS) inhibitor, or a drug candidate targeting mutant IDH1, mutant IDH2, the mitochondrial one-carbon pathway, or ATP citrate lyase.

GLS is an amidohydrolaze that generates glutamate from glutamine. GLS exists in two isoforms GLS1 and GLS2 (initially identified as kidney and liver glutaminase, respectively). GLS1 has two splice variants, kidney type glutaminase (KGA) isoform and glutaminase C (GAC) isoform, which are both located in the mitochondria. GLS1 expression and elevated glutamine uptake has been described in many tumors and therefore glutaminase can be a viable target in treating cancer patients by monotherapy or in combination with other treatments.

In another preferred embodiment, the treatment response of the cancer cells to a drug affecting a metabolic pathway is predicted in step e) based on a metabolic dependency of the cancer cells shown by the results obtained in step d). Preferably, said cancer cells are found to be dependent on glutamine.

In another preferred embodiment, the aggressiveness of the cancer cells is assessed in step e) based on the metabolic activity of the cancer cells shown by the results obtained in step d) so that metabolically more active cells correspond to an aggressive cancer, and metabolically less active cells correspond to less aggressive cancer. Elevated metabolic activity is indicative of increased proliferation and increased malignancy.

In a further preferred embodiment, the method comprises a step of treating said patient according to the results obtained in step e).

Otto Warburg observed in the beginning of the last century that tumors exhibit elevated glycose uptake and glycolysis. Warburgs' initial explanation, that it was caused by permanently impaired mitochondrial OXPHOS, has been challenged by later studied which have shown that the function of mitochondrial OXPHOS is intact in most spontaneous cancers. In addition, it has been shown that mitochondria have pivotal role in cancer initiation, maintenance and progression via OXPHOS, but importantly, also via many metabolic adaptations. Studying mitochondrial metabolism on intracellular level has remained complicated due to metabolic compartmentalization and due to very limited applicability of standard methods in human subjects. The method described here solves many of those issues.

DETAILS OF THE PREFERRED EMBODIMENTS

Preferably, the method of the present invention consists of the following general outline (see FIG. 1):
1. Sample collection.
2. Sample preparation.
3. Induction phase. Induction reactions in a measurement chamber.
4. Collection of reaction medium and separation of the sample from it. Isolated processing of the sample if necessary.
5. Analytical phase. Analysis of reaction medium (for specific metabolites or other biological substances originating from the sample that are present in the reaction medium as a results of the induction phase). Analysis is done in the device used for induction reaction if possible, but it can also be done in separate machine/machines to detect and quantify desired biologically relevant compounds available in the reaction medium.
6. Interpretation phase. This step is for interpretation of the results. In some embodiments, the result is usable for stratifying patients based on their suitability for specific treatments or for quantifying metabolic activity of a given sample (e.g. aggressiveness of a tumor).

The method of the present invention can be used irrespective of cell preparation method (including cell culture growing time or conditions). Some examples of sample collection and preparation of the cells are described in the Examples section of this document. Tissue fiber samples originating from healthy or diseased source are collected into storing medium as soon as possible after the sample is harvested to ensure viability of the sample. Storing medium can have composition as in Lahus-A (see Examples), but other compositions or preservation methods (like cryopreservation) can be used with the main aim to maintain viability of the sample until it is used for further analysis. Collected samples in Lahus-A are preferably processed further within 0-6 hours after harvesting the tissue sample. The samples can be frozen for extending the time between harvesting and analysis. In case blood samples are used, longer transport time is acceptable if maximum viability of the sample is warranted using suitable collection and transport methods.

In induction phase, a device with a measurement chamber, where constant temperature can be hold (preferably not changing more than +/−5 degrees Centigrade during any ongoing experiment; preferred temperature is in the range from 10-41 degrees centigrade with one optimum at 25 degrees Centigrade) is preferably used. In some embodiments, hermetic isolation can be used for the analysis chamber to define the initial amount of gases in the reaction chamber (e.g. define and measure the initial concentration of oxygen and if the device allows, measure the change in oxygen concentration over the course of the measurement). In some embodiments, also open reaction chambers can be used so that gases in the reaction chamber are always in direct interaction with the atmospheric gases. In some embodiments, it is advantageous to introduce new compounds to the reaction medium during the course of a test. These added compounds can be specific metabolic inhibitors (inhibitors of enzymes facilitating chemical reactions, or facilitating metabolite transport between intracellular compartments, in some embodiments these inhibitors can be drugs, drug candidates or other biologically active compounds). In some embodiments, it is necessary to stir the reaction medium via internal magnetic stirrer or placing vials with the reaction medium into a stirring device that is able to stir and heat the reaction medium without a need to introduce solid bodies to the reaction medium for stirring.

Possible devices for the induction phase can be: 1) OROBOROS Oxygraph-2k (O2k), O2k-Fluorometer (OROBOROS O2k-Fluorometer, OROBOROS Oxygraph-2k Fluorometer), or any other respirometer sold by OROBOROS INSTRUMENTS Corp.; 2) Any Seahorse Analyzer, respirometer or device for making temporal measurements on cells, as sold by Agilent Technologies; 3) Any other commercial or non-commercial device that comprises of a measuring chamber (for liquids; device can have one or more chambers or can be multi-well plate) with ability to control temperature. In some embodiments, this device or its reaction chamber can be sealed off hermetically from the atmosphere. In some embodiments, this device can measure florescence or UV radiation descriptive for manipulations on the sample in the reaction chamber before or during the measurement. In some embodiments, this device is equipped with sensors for measuring pH inside the reaction chamber.

The present method requires permeabilization of the cells or fibers in order to remove the barrier between cell internal compartment and the reaction medium surrounding the samples. Permeabilization agent is preferably used to make holes in the cells membrane so that cell internal membranes stay intact (internal organelles with membranes including mitochondria, nucleus, chloroplasts or peroxisomes). Permeabilization facilitates free movement of chemicals or biological compounds in and out from the cell structure, while internal structures of the cells stay intact—this allows to measure function and metabolic activity of intracellular organelles (with membranes) without disturbing the intracellular architecture and physical connections. Permeabilization is preferred over the isolation of mitochondria due to the benefits described above, but also, because amount of sample is significantly smaller if permeabilization technique is used. Isolated mitochondria are not representative of the cells they were isolated from due to loss of intracellular structure, which, in part, drives the function of mitochondria.

Permeabilization can be done in at least two following ways:
i) Cells or fibers are exposed to permeabilization agent (dissolved in suitable medium in order to maintain viability of the intracellular intact organelles), incubation time of 0-30 minutes is allowed and thereafter standard incubation procedure is started.
ii) Cells or fibers are exposed to the permeabilization agent and incubation time of 0-30 minutes is allowed. The resulting cells or fibers are washed several times with suitable solution (to maintain viability of intact intracellular organelles), preferably 1-5 times, to remove all soluble content besides the permeabilized cells or fibers. The resulting cells or fibers are then used for standard induction procedure and in such case, all cytosolic soluble ensymes and metabolites are removed and do not interfere with the measurement.

Choice of either of the permeabilization approaches depends on the target of a given experiment or test.

Permabilization agent concentration is defined via prior testing. Target for the initial tests is to define optimal concentration for the permeabilization agent so that cell membrane is permeabilized, but quality control markers are not showing damage to intracellular organelles with membranes. Suitable concentration of permeabilization agent is preferably defined for each tissue and sample types and quantities so that it is not necessary to confirm the permeabilization agent concentration prior to each test. In routine testing of the same sample types, intactness of internal membranes (e.g. mitochondrial inner and outer membrane), as part of quality control, is confirmed via addition of different inhibitors and measuring or assessing their effect thereafter. See Examples.

Reaction medium for the induction phase can have the composition as in Lahus-B (see Examples). Preferred temperature of the reaction medium during testing is 25 degrees centigrade. Possible substrate combinations for the induction phase are listed in Table 1.

TABLE 1

Possible substrate combinations (not restrictive for the use of the test; in addition to reaction medium) and possible metabolites to quantify in the analytical phase.

| # Substrates* | Target metabolites |
|---|---|
| 1. Glutamate, malate | Quantification of any or |
| 2. Pyruvate, malate | combination of the following |
| 3. Succinate, malate | metabolites in the reaction |
| 4. Palmitoylcarnitine, malate | medium or in the sample as |
| 5. Glutamate, pyruvate, palmitoylcarnitine, malate | the result of the test in the induction phase, including, |
| 6. Glutamine, malate | but not restricted to: |
| 7. Ornithine, malate | citrate, alpha-ketoglutarate, |
| 8. Arginine, malate | pyruvate, palmitoylcarnitine, |
| 9. Formate, malate, or any other metabolite or metabolites facilitating one-carbon metabolism measurement | folate, ATP, ADP, citrulline, ornithine, oxaloacetate, δ-aminolevulinic acid, alanine, arginine, asparagine, aspartate, |
| 10. Proline, malate | cysteine, glutamine, glutamate, |
| 11. Membrane transport inhibitors** like, but not restricted to, 1,2,3-benzenetricarboxylic acid, UK5099, atractylate, mersalyl, butyl malonate, phenyl succinate, cyano-OH-cinnamate | glycine, histidine, isoleucine, leucine, lysine, methionine, proline, serine, threonine, tryptophan, phenylalanine, tyrosine, valine, $H_2O_2$, carnitine, phosphoenolpyruvate, formate, |
| 12. Other inhibitors like, but not restricted to: BMS303141, BPTES, AG-120, AG-221, AG-881, CB-839, BAY1436032, FT-2102, GSK321, IDH305 | fumarate, succinate, iso-citrate, RNA, urea, 2-hydroxyglutarate. |
| 13. Exogenous enzymes to improve test accuracy or facilitate reactions of interest, including, but not restricted to: IDH1, IDH2, IDH3, ACLY, mutant IDH1, mutant IDH2, malic enzyme | |

*Any of these substrates can be isotope-labelled to trace metabolic pathways.
**Membrane transport inhibitors are used to isolate specific sources for metabolite flux (either into or from mitochondria or relating to other intracellular organelles with membranes). These specific fluxes can be accompanied with suitable selection of metabolic substrates.

After the induction phase, the sample is removed from the reaction medium after the induction phase has been deemed to be finished. The reaction medium can be centrifuged in laboratory centrifuge (preferably at 4 degrees Centigrade; up to 10 minutes at 14000 rpm) and/or syringe filters can be used to remove debris from the reaction medium. Purified supernatant should be stored on ice for further processing or stored below −40 degrees centigrade for processing later. In some embodiments, it is preferred to rapidly stop the induction phase by adding cold methanol or any other compound or compounds that inhibit or stop any biological activity in the reaction medium.

The aim of the induction phase is to accumulate metabolites into the reaction medium, which can thereafter be analyzed further to quantify the metabolite fluxes. In some embodiments, the sample is used for further processing to detect concentrations of metabolites in the sample intracellular organelles. Once the induction phase has been termed to be over, the sample must be removed from the reaction medium immediately to stop any further biological activity in the reaction medium. If skinned fibers are used, the fiber must me physically removed from the reaction medium, the reaction medium can be centrifuged to concentrate any debris in the reaction medium and the resulting supernatant can be used for further processing. If cells are used, the reaction medium must be centrifuged immediately after the end of the induction phase and the supernatant can be used for further analysis. In some embodiments, the supernatant (for both fibers and cells) can be filtered using a syringe filter to remove contaminating particles. Additional chemical compounds can be used to stop any biological activity in the end of the induction phase or to isolate metabolites based on solubility in different solvents. The collected supernatant should be stored on ice for further processing. If needed, after the induction phase, the supernatant or the samples can be frozen as soon as possible after the supernatant is collected (sample should be frozen preferably below 40 degrees Celsius).

In the analytical phase, any analytical device or method can be used to quantify metabolite levels in the reaction medium or in the samples after the induction phase is over and the reaction medium and the sample are collected separately. Analytical device is selected based on which metabolites are to be quantified and which device is suitable for doing such measurements (including UV-VIS, NMR, or quantitative or semi-quantitative measurements using MS devices).

The aim of the test is to expose the sample to such conditions that the fluxes from intracellular compartments can be harvested later from the reaction medium. In such situation, the intracellular organelles with membranes exchange metabolites with its surrounding environment (reaction medium) and the accumulated metabolites can be quantified in the end of the induction phase so that the standard biological processes normally present in the cytosol are eliminated and do not consume or synthesise the compounds that were introduced to the reaction medium or were effluxed by intracellular organelles. In such conditions, specific metabolite fluxes can be restricted to specific intracellular organelles.

In analytical phase, any analytical device or method can be used to quantify the metabolites of interest in the reaction medium. Both accumulation and decrease of metabolites can be measured. See Examples.

Further Embodiments

As further preferred embodiments, the present invention is also directed to a method for quantifying time dependent intracellular metabolite fluxes in permeabilized cells or fibers, the method comprising:
   a. a temperature controlled container for housing reaction medium and the sample;
   b. reaction medium to facilitate permeabilization (using electro-permeabilization, compounds like, but not restricted to, saponine, digitonin or pore-forming toxins) of the sample and maintaining maximum viability of the intracellular organelles with membranes not terminally affected by the permeabilization, if the permeabilization is not executed before introducing the sample to the measurement container;
   c. reaction medium in the reaction container maintaining viability of the sample during the test and allowing accumulation of metabolites;
   d. selection of substrates and/or inhibitors in the reaction medium (c) to quantify one or more fluxes of interest;

e. induction phase lasting from 0.1-180 minutes in presence of reaction medium (c) and selected substrates (d) to allow biologic activity of intracellular organelles and accumulation of metabolites to the reaction medium;

f. analytical phase for quantifying metabolites dissolved to the reaction medium as a result of the induction phase (e);

g. calculations to quantify amounts of metabolites accumulated to the reaction medium during the induction phase (e) and quantified during analytical phase (f), normalized to sample;

h. comparison of calculation results (g) to database of equal measurements on samples of the same type to detect the position of current test results in the prior datasets;

i. assessment of clinical relevance of the test results (h) to differentiate the given sample from other equal samples based of metabolic activity i.e. aggressiveness of the given sample (e.g. aggressiveness of a human tumor);

j. assessment of clinical relevance of the test results (h) to predict treatment response to drugs, drug candidates or biologically active compounds affecting the pathway or pathways quantified as the result of the given test or facilitating the pathway of interest in terms of the inhibitor target;

Preferably, the above method is for use in medical oncology or other medical fields, to differentiate metabolically more active i.e. aggressive samples (e.g. tumors) from less active i.e. less aggressive samples (e.g. tumors), comprising of time dependent quantification of metabolite of interest and comparing the results to dataset of results of equal samples, quantified metabolites comprising:

a. Citrate efflux from mitochondria or other intracellular organelles without the presence of membrane bound citrate carrier inhibitor (inhibitor like 1,2,3-benzenetricarboxylic acid or other inhibitors equal to its inhibitory effect);

b. Alpha-ketoglutarate efflux from mitochondria or other intracellular organelles without the exogenous addition of compounds inhibiting its efflux to the reaction medium;

c. Pyruvate efflux from mitochondria or other intracellular organelles without the exogenous addition of compounds inhibiting its efflux to the reaction medium;

d. Glutamate or glutamine efflux from mitochondria or other intracellular organelles without the exogenous addition of compounds inhibiting its efflux to the reaction medium;

e. Oxaloacetate efflux from mitochondria or other intracellular organelles without the exogenous addition of compounds inhibiting its efflux to the reaction medium;

f. Serine, aspartate and/or formate efflux from mitochondria or other intracellular organelles without the exogenous addition of compounds inhibiting its efflux to the reaction medium;

g. Combination of one or more of the here mentioned metabolite effluxes from mitochondria or other intracellular organelles without the exogenous addition of compounds inhibiting its efflux to the reaction medium, selection of metabolites comprising, in addition, but not restricted to:

i. Malate, palmitoylcarnitine, folate, ATP, ADP, citrulline, ornithine, δ-aminolevulinic acid, alanine, arginine, asparagine, cysteine, glutamine, glycine, histidine, isoleucine, leucine, lysine, methionine, proline, threonine, tryptophan, phenylalanine, tyrosine, valine, H2O2, carnitine, phosphoenolpyruvate, fumarate, succinate, iso-citrate, RNA, urea, 2-hydroxyglutarate.

h. Decrease in any of the above mentioned metabolites in the reaction medium if it was added exogenously or its concentration was measured during the induction phase.

Preferably the above method is for use in medical oncology or other medical fields, to differentiate metabolically more active i.e. aggressive samples (e.g. tumors) from less active i.e. less aggressive samples (e.g. tumors) as described in above, comprising additionally:

a. In addition to free accumulation test conducted as described above, additional test, if needed, can be conducted as described above in the presence of one or more specific inhibitors (of enzymes, transporters or other biological compounds facilitating flux of metabolite or metabolites of interest) to eliminate and define sources or pathways of metabolite efflux.

Preferably the above method is for use in medical oncology or in other medical fields, to stratify patients based on expected response to metabolic inhibitors (drugs, drug candidates or other biologically active compounds), comprising of time dependent quantification of metabolite of interest and comparing the results to dataset of results of equal samples and their known medical outcomes, quantified metabolites comprising:

a. Citrate efflux from mitochondria or other intracellular organelles without the presence of membrane bound citrate carrier inhibitor (inhibitor like 1,2,3-benzenetricarboxylic acid or other inhibitors equal to its inhibitory effect);

b. Alpha-ketoglutarate efflux from mitochondria or other intracellular organelles without the exogenous addition of compounds inhibiting its efflux to the reaction medium;

c. Pyruvate efflux from mitochondria or other intracellular organelles without the exogenous addition of compounds inhibiting its efflux to the reaction medium;

d. Glutamate or glutamine efflux from mitochondria or other intracellular organelles without the exogenous addition of compounds inhibiting its efflux to the reaction medium;

e. Oxaloacetate efflux from mitochondria or other intracellular organelles without the exogenous addition of compounds inhibiting its efflux to the reaction medium;

f. Serine, aspartate and/or formate efflux from mitochondria or other intracellular organelles without the exogenous addition of compounds inhibiting its efflux to the reaction medium;

g. Combination of one or more of the here mentioned metabolite effluxes from mitochondria or other intracellular organelles without the exogenous addition of compounds inhibiting its efflux to the reaction medium, selection of metabolites comprising, in addition, but not restricted to:

i. Malate, palmitoylcarnitine, folate, ATP, ADP, citrulline, ornithine, δ-aminolevulinic acid, alanine, arginine, asparagine, cysteine, glutamine, glycine, histidine, isoleucine, leucine, lysine, methionine, proline, threonine, tryptophan, phenylalanine, tyrosine, valine, H2O2, carnitine, phosphoenolpyruvate, fumarate, succinate, iso-citrate, RNA, urea, 2-hydroxyglutarate;

h. Decrease in any of the above-mentioned metabolites in the reaction medium if it was added exogenously or its concentration was measured during the induction phase.

Preferably, the above method is for use in medical oncology or other medical fields, to stratify patients based on expected response to metabolic inhibitors (drugs, drug candidates or other biologically active compounds) as described above, comprising additionally:

a. In addition to free accumulation test conducted as described under claim 4, additional test, if needed, can be conducted as described in claim 1 and claim 4 in the presence of one or more specific inhibitors (of enzymes, transporters or other biological compounds facilitating flux of metabolite or metabolites of interest) to eliminate and define sources or pathways of metabolite efflux.

Preferably, the above method is for use in clinical context as described in above, comprising, if deemed necessary:

a. Exogenously added enzyme, enzymes, chemical compounds or other biologically active substances to simulate or accentuate pathway or cytosolic effects that are not present in the sample during the induction phase or are present at unsatisfactory activity.

The publications and other materials used herein to illuminate the background of the invention, and in particular, to provide additional details with respect to its practice, are incorporated herein by reference. The present invention is further described in the following Examples, which are not intended to limit the scope of the invention.

EXAMPLES

Example 1. Temporal Quantification of Citrate and Amino Acids from MCF-7 Culture Cells Experiments were performed on human breast cancer cells of the line MCF-7 to quantify mitochondrial citrate efflux in presence of different metabolic substrates.

1. Experimental Procedures 1.1. Preparation of Cells

Stock culture of MCF-7 cells was obtained from American Type Culture Collection (ATCC® Number: HTB-22™). The cells were grown as adherent monolayers in big T75 flasks (Greiner Bio-One GmbH, Germany) in low glucose (1.0 g/L) DMEM with stable L-glutamine (PAA Laboratories GmbH, Austria) that was supplemented with 1 mM Na-pyruvate (Gibco®, REF 11360-039), 10% heat-inactivated fetal bovine serum (FBS), 10 pg/mL human recombinant insulin (Gibco) and antibiotics: penicillin (100 U/ml), streptomycin (100 µg/ml) and gentamicin at a final concentration of 50 µg/ml. MCF-7 cells were grown and maintained at 37° C. in a humidified incubator containing 5% CO2 in air. The cells were sub-cultured at 2-3 day intervals.

MCF-7 cells were harvested from 5 T75 flasks (72 h after their seeding at a subculturing ratio of 1/5) by means of accutase (a cell detachment agent) treatment.

After detachment, the cell were washed twice with Mitomed-B solution (see Table 2), supplemented with lmg/ml bovine serum albumin (BSA) and 3-5 µM leupeptin (protease inhibitor) with centrifugation (on a Heraus "Biofuge primo R" refrigerated centrifuge equipped with a swing-out rotor, 150×g for 7 min at 4° C.). After washing, the pellet was resuspended in 2.5 ml of Mitomed-B (supplemented with lmg/ml BSA and 3-5 µM leupeptin) and the cells were stored on melting ice.

The number of MCF-7 cells in suspension (N) was measured by a hemocytometer (Goryaev's chamber) after 20-fold dilution by Mitomed B (cells in 15 small chambers were counted): $N=(91+97+86)/3 \times 15 \times 1111 \times 20 = 30.44 \times 10^6$ cells/ml.

In addition, aliquots (0.1 ml) of the cell suspension and Mitomed-B solution were collected for measuring protein content.

TABLE 2

Chemical Composition of Mitomed B (pH 7.1 at 25° C.).

| Compound | Final concentration, mM |
|---|---|
| EGTA | 0.5 |
| $MgCl_2 * 6H_2O$ | 3 |
| $KH_2PO_4$ | 3 |
| Taurine | 20 |
| HEPES | 20 |
| Sucrose | 110 |
| DTT | 0.5 |
| K-Lactobionate | 60 |
| BSA, fraction V, fatty acid free | 1 mg/ml |

2. Induction Phase

The experiments were carried out in an Oroboros oxygraph. Two parallel chambers on the same device were used. Reaction medium was Lahus-B as described below (Table 3).

TABLE 3

Chemical composition of "Lahus B".

| Substances | Final concentration, mM |
|---|---|
| Imidasool | 20 |
| $KH_2PO_4$ | 3 |
| Dithiothreitol | 0.5 |
| Tauriin | 20 |
| $MgCl_2 \times 6H_2O$ | 4 |
| MES** | 100 |
| $K_2Ca$-EGTA | 2.74 |
| $K_2$-EGTA | 4.72 |
| BSA | 1 mg/ml |

**MES is 2-morpholinoethanesulfonic acid monohydrate.

TABLE 4

Protocols for sets of substrates to be added to the reaction medium Lahus-B. Concentration is given as the final concentration in the reaction medium.

| 1 | 2 | 3 | 4 |
|---|---|---|---|
| Glutamate, 5 mM | Glutamate, 5 mM | Pyrvate, 0.05 mM | Pyrvate, 0.05 mM |
| SAMPLE | SAMPLE | SAMPLE | SAMPLE |
| BMS303141, 8 µM | BMS303141, 8 µM | BMS303141, 8 µM | BMS303141, 8 µM |
| Saponine, 30 µg/ml | Saponine, 30 µg/ml | Saponine, 30 µg/ml | Saponine, 30 µg/ml |
| — | 1,2,3-BTC, 1 mM | — | 1,2,3-BTC, 1 mM |
| ADP, 2 mM | ADP, 2 mM | ADP, 2 mM | ADP, 2 mM |
| Cytochrome c, 8 µM | Cytochrome c, 8 µM | Cytochrome c, 8 µM | Cytochrome c, 8 µM |
| CAT, 1 µM | CAT, 1 µM | CAT, 1 µM | CAT, 1 µM |

| 5 | 6 | 7 | 8 |
|---|---|---|---|
| PalCar, 40 µM | PalCar, 40 µM | Succinate, 10 mM | Succinate, 10 mM |
| SAMPLE | SAMPLE | SAMPLE | SAMPLE |
| BMS303141, 8 µM | BMS303141, 8 µM | BMS303141, 8 µM | BMS303141, 8 µM |
| Saponine, | Saponine, | Saponine, | Saponine, |

TABLE 4-continued

Protocols for sets of substrates to be added to the reaction medium Lahus-B.
Concentration is given as the final concentration in the reaction medium.

| 30 µg/ml<br>—<br>ADP, 2 mM<br>Cytochrome c,<br>8 µM<br>CAT, 1 µM | 30 µg/ml<br>1,2,3-BTC, 1 mM<br>ADP, 2 mM<br>Cytochrome c,<br>8 µM<br>CAT, 1 µM | 30 µg/ml<br>—<br>ADP, 2 mM<br>Cytochrome c,<br>8 µM<br>CAT, 1 µM | 30 µg/ml<br>1,2,3-BTC, 1 mM<br>ADP, 2 mM<br>Cytochrome c,<br>8 µM<br>CAT, 1 µM |
|---|---|---|---|

Palmitoylcarnitine (Palcar), 1,2,3-benzenetricarboxylic acid (1,2,3-BTC), carboxyatracty Saponine concetration suitable for viability of MCF-7 cells was defined as 30 µg/ml. Malate, 2 mM, was present in all protocols in the reaction medium. BMS303141 was used to inhibit activity of ATP-citratelyase to stop it from metabolizing free citrate that accumulates to the reaction medium. 1,2,3-benzenetricarboxylic acid was used to stop citrate efflux from mitochondria. Saponine incubation time was 5 minutes. Cytochrome c and CAT were injected to the reaction medium right at the end of the experiment to assess the quality of mitochondrial inner and outer membranes.

On 20 May 2015 the following substrate protocols were tested: 1, 2, 3, 4, 5, 6.

Duration of the induction phase: 1 hour.

3. Collection of the Reaction Medium

Once the induction phase was ended, the reaction medium was transferred to 2 ml Eppendorf tube for centrifugation (14 000 rpm, 7 minutes). The supernatant was collected through syringe filter and stored on ice. Cell pellet was discarded as biological waste.

4. Analytical Phase

900 µl of each supernatant was used to enzymatically measure concentration of citrate as described before (Petrarulo et al, 1995).

100 µl was used to measure amino acid concentrations using Acquity UPLC (Waters Corp., Milford, Mass., USA) according to manufacturers' instructions.

5. Results

Figure 3:
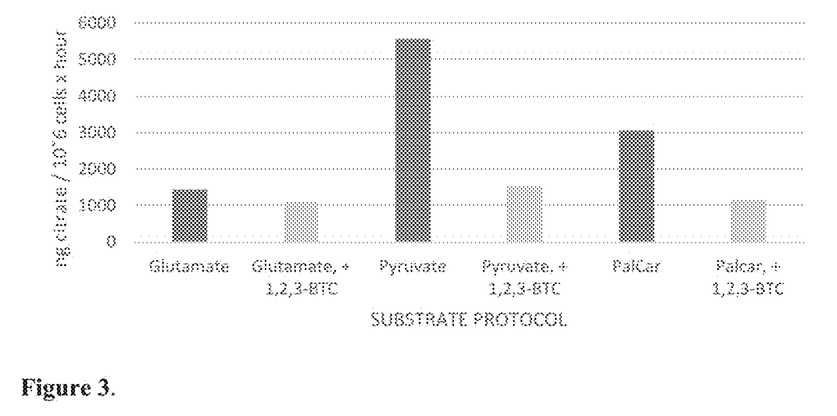
FIG. 3. Efflux of citrate from permeabilized MCF-7 cells based on different substrate protocols.

Citrate efflux results are presented in the table below and on FIG. 3.

TABLE 5

Results for citrate efflux from permeabilized MCF-7 cells.

| # | Protocol | Protocol, main substrate | cells/ml | ng citrate per 10^6 cells per hour |
|---|---|---|---|---|
| 1 | 1 | Glutamate | 4.56 × 10^6 | 1428 |
| 2 | 2 | Glutamate, + 1,2,3-BTC | 4.56 × 10^6 | 1098 |
| 3 | 3 | Pyruvate | 4.56 × 10^6 | 5564 |
| 4 | 4 | Pyruvate, + 1,2,3-BTC | 4.56 × 10^6 | 1524 |
| 5 | 5 | PalCar | 4.56 × 10^6 | 3059 |
| 6 | 6 | Palcar, + 1,2,3-BTC | 4.56 × 10^6 | 1156 |

It is evident that citrate efflux in these cells is mainly originating from exogenous pyruvate or palmitoylcarnitine. Citrate efflux based on glutamate as substrate is very low and very close to the value when citrate transport to the reaction medium was inhibited by 1,2,3-BTC.

TABLE 6

Amino acid efflux from permeabilized MCF-7 cells, values
are ng amino acid per 10^6 cells per hour.

| Protocol | 3 | 4 | 5 |
|---|---|---|---|
| Ala | 472 | 459 | 364 |
| Arg | — | — | — |
| Asn | — | — | — |
| Asp | 910 | 671 | 735 |
| Cys | — | — | — |
| Gln | — | — | — |
| Glu | 1115 | 1235 | 1364 |
| Gly | 1249 | 1387 | 1418 |
| His | — | — | — |
| Ile | — | — | — |
| Leu | — | — | — |
| Lys | — | — | — |
| Met | — | — | — |
| Orn | — | — | — |
| Phe | — | — | — |
| Pro | 411 | 409 | 434 |
| Ser | 227 | 217 | 207 |
| Thr | 725 | 758 | 779 |
| Trp | — | — | — |
| Tyr | — | — | — |
| Val | — | — | — |

Above are the results for amino acid measurement via UPLC. Values are not given if the value was below detection limit. Only free amino acids were measured in the reaction medium.

Example 2. Detection of Citrate Efflux Dynamics in MDA-MB-231 Culture Cells

1. Experimental Procedures 1.1. Preparation of Cells

Stock culture of MDA-MB-231 cells was obtained from American Type Culture Collection (ATCC® Number: HTB-26™). These cells were grown, harvested, washed and stored for analysis as described in Example 1.

The number of MDA-MB-231 cells in suspension (N) was measured by a hemocytometer (Goryaev's chamber) after 20-fold dilution by Mitomed B (cells in 15 small chambers were counted): N=(23+26+27+32+31)/5×15×1111×20=9.27×10^6 cells/ml.

In addition, aliquots (0.1 ml) of the cell suspension and Mitomed-B solution were collected for measuring protein content.

2. Induction Phase

The experiments were carried out in an Oroboros oxygraph. Two parallel chambers on the same device were used. Reaction medium was Lahus-B (Table 3).

Saponine concetration suitable for viability of MDA-MB-231 cells was defined as 30 µg/ml. Malate, 2 mM, was present in all protocols in the reaction medium. BMS303141 was used to inhibit activity of ATP-citrate lyase to stop it from metabolizing free citrate that accumulates to the reaction medium. 1,2,3-benzenetricarboxylic acid was used to stop citrate efflux from mitochondria. Saponine incubation time was 5 minutes. Cytochrome c and CAT were injected to the reaction medium right at the end of the experiment to assess the quality of mitochondrial inner and outer membranes.

TABLE 7

Protocol for set of substrates to be added to the reaction medium Lahus-B. Concentration is given as the final concentration in the reaction medium.

| # | Compound |
|---|---|
| 1 | Glutamate, 5 mM |
| 2 | SAMPLE |
| 3 | BMS303141, 8 µM |
| 4 | Saponine, 30 µg/ml |
| 5 | ADP, 2 mM |
| 6 | Cytochrome c, 8 µM |
| 7 | Carboxyatractyloside, 1 µM |

Duration of the induction phase: the induction time for 4 different tests were 10, 20, 40 and 60 minutes to detect dynamics in citrate efflux.

3. Collection of the Reaction Medium

Once the induction phase was ended, the reaction medium was transferred to 2 ml Eppendorf tube for centrifugation (14 000 rpm, 7 minutes). The supernatant was collected through syringe filter and stored on ice. Cell pellet was discarded as biological waste.

4. Analytical Phase

900 µl of each supernatant was used to enzymatically measure concentration of citrate as described before (Petrarulo et al, 1995).

5. Results

Figure 4:
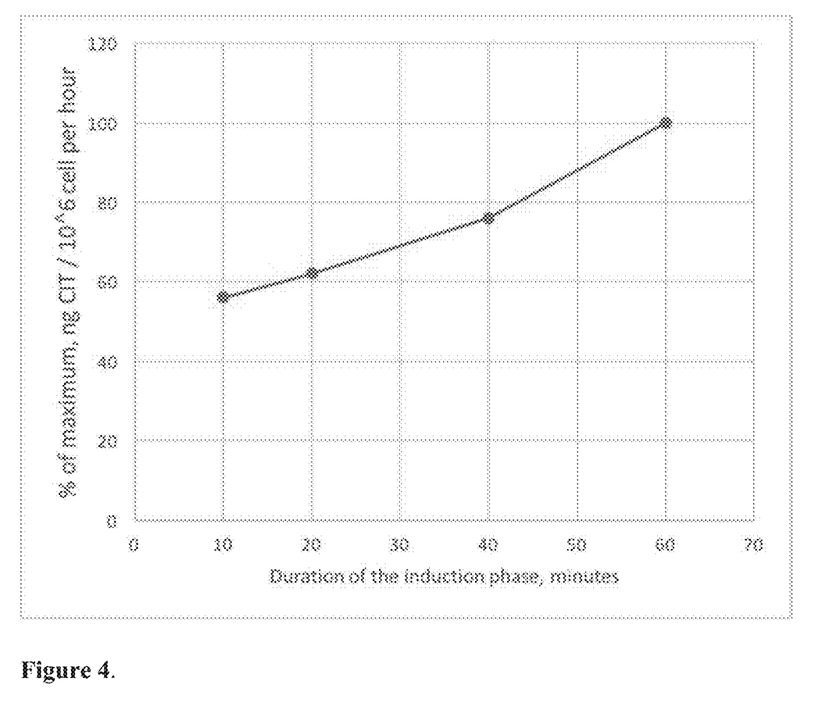
FIG. 4. Dynamics of the citrate efflux from permeabilized MDA-MB-231 cells.

It can be concluded the accumulation of citrate in the reaction medium does not reach saturation (see FIG. 4).

Example 3. Temporal Quantification of Citrate from Human Breast Cancer Samples Experiments were performed on permeabilized skinned fibers derived from human breast cancer cells to quantify temporal citrate efflux.

1. Experimental Procedures 1.1. Preparation of Fibers

In order to reach experiment targets, the sarcolemma and plasma membranes in skinned tumor fibers were completely permeabilized by saponin treatment keeping the mitochondrial membranes intact (both tumor and healthy tissue samples from the same patient were processed equally). Namely, skinned fibers were transferred into plastic vials with pre-cooled (on ice) Lahus-A (Table 8) containing 50 µg/ml saponin and incubated with mild stirring (at 40 rpm) for 30 min at 4° C. Permeabilized fibers were then washed in pre-cooled solution Lahus-B (Table 3) for 5 min under mild stirring; this washing procedure was performed three times to completely remove saponin and all soluble metabolites. The washed samples were placed into Lahus-B (Table 3) and kept in the same medium (at 4° C.) until use.

TABLE 8

Chemical composition of Lahus-A.

| Chemicals | Concentrations, mM |
|---|---|
| $KH_2PO_4$ | 3 |
| Dithiothreitol (DTT) | 0.5 |
| Taurine | 20 |
| ATP | 5.3 |
| Phosphocreatine | 15 |
| $MgCl_2 \times 6H_2O$ | 9.5 |
| MES* | 82.9 |
| $K_2EGTA$ | 1 |

*MES is 2-morpholinoethanesulfonic acid monohydrate.

2. Induction Phase

The experiments were carried out in an Oroboros oxygraph. Two parallel chambers on the same device were used. Reaction medium was Lahus-B (Table 3). Substrates introduced into the reaction medium Lahus-B were as are indicated in Table 9.

TABLE 9

Protocols for sets of substrates to be added to the reaction medium Lahus-B. Concentration is given as the final concentration in the reaction medium.

| 1 | 2 | 3 | 4 |
|---|---|---|---|
| Glutamate, 5 mM | Glutamate, 5 mM | Pyrvate, 0.05 mM | Pyrvate, 0.05 mM |
| SAMPLE | SAMPLE | SAMPLE | SAMPLE |
| BMS303141, 8 µM | BMS303141, 8 µM | BMS303141, 8 µM | BMS303141, 8 µM |
| — | 1,2,3-BTC, 1 mM | — | 1,2,3-BTC, 1 mM |
| ADP, 2 mM | ADP, 2 mM | ADP, 2 mM | ADP, 2 mM |
| Cytochrome c, 8 µM | Cytochrome c, 8 µM | Cytochrome c, 8 µM | Cytochrome c, 8 µM |
| CAT, 1 µM | CAT, 1 µM | CAT, 1 µM | CAT, 1 µM |

| 5 | 6 |
|---|---|
| PalCar, 40 µM | PalCar, 40 µM |
| SAMPLE | SAMPLE |
| BMS303141, 8 µM | BMS303141, 8 µM |
| — | 1,2,3-BTC, 1 mM |
| ADP, 2 mM | ADP, 2 mM |
| Cytochrome c, 8 µM | Cytochrome c, 8 µM |
| CAT, 1 µM | CAT, 1 µM |

Palmitoylcarnitine (Palcar), 1,2,3-benzenetricarboxylic acid (1,2,3-BTC), carboxyatractyloside (CAT).

Saponine concetration suitable for viability of skinned breast cancer fibers was defined as 50 µg/ml. Malate, 2 mM, was present in all protocols in the reaction medium. BMS303141 was used to inhibit activity of ATP-citrate lyase to stop it from metabolizing free citrate that accumulates to the reaction medium. 1,2,3-benzenetricarboxylic acid was used to stop citrate efflux from mitochondria. Cytochorome c and CAT were injected to the reaction medium right at the end of the experiment to assess the quality of mitochondrial inner and outer membranes.

All samples were weighted before transferring these to the reaction medium. Sample weight can be 0-200 mg (preferably between 15-75 mg) per reaction in an Oroboros oxygraph.

Duration of the induction phase: 1 hour.

3. Collection of the Reaction Medium

Once the induction medium was ended, the reaction medium was transferred to 2.5 ml Eppendorf tube for centrifugation (14 000 rpm, 7 minutes). Fiber was removed from the reaction medium and weighted for calculations. The supernatant from the centrifugation was collected through syringe filter and stored on ice. Remaining debris was discarded as biological waste.

4. Analytical Phase

900 µl of each supernatant was used to enzymatically measure concentration of citrate as described before (Petrarulo et al, 1995).

100 µl of each supernatant was frozen to be used to measure amino acid concentrations using Acquity UPLC (Waters Corp., Milford, Mass., USA) according to manufacturers' instructions.

5. Results

Citrate efflux from the permeabilized human breast cancer and healthy tissue fibers are indicated below.

TABLE 10

Experiment results from permeabilized fibers derived from human breast cancer clinical sample (including adjacent healthy tissue samples).

| Protocol | Protocol, name | Sample | Sample weight, mg | ng citrate/ mg × 60 min | $O_2$ concentration (nmol/ml) Start | End |
|---|---|---|---|---|---|---|
| 1 | Glut/Mal | Cancer | 67.90 | 144.1 | 194 | 0 |
| 2 | Glut/Mal, + 1,2,3-BTC | Cancer | 62.50 | 41.7** | 208 | 5 |
| 1 | Glut/Mal | Cancer | 56.20 | 172.1 | 225 | 18 |
| 1 exp (-ADP) | Glut/Mal, -ADP* | Cancer | 55.30 | 67.7 | 229 | 84 |
| 3 | Pyr/Mal | Cancer | 57.30 | 194.6 | 208 | 12 |
| 4 | Pyr/Mal, +1,2,3_BTC | Cancer | 67.80 | 17.6** | 201 | 13 |
| 5 | Palcar/Mal | Cancer | 58.00 | 158.7 | 218 | 0 |
| 6 | Palcar/Mal, +1,2,3_BTC | Cancer | 55.50 | 73.7 | 228 | 10 |
| 1 | Glut/Mal | Healthy tissue | 58.30 | 38.5** | 244 | 191 |
| 2 | Pyr/Mal | Healthy tissue | 70.80 | 49.9** | 244 | 190 |

*Experimental procedure to define if the induction process is ADP-dependent.
**Results below detection limit.

Figure 5:
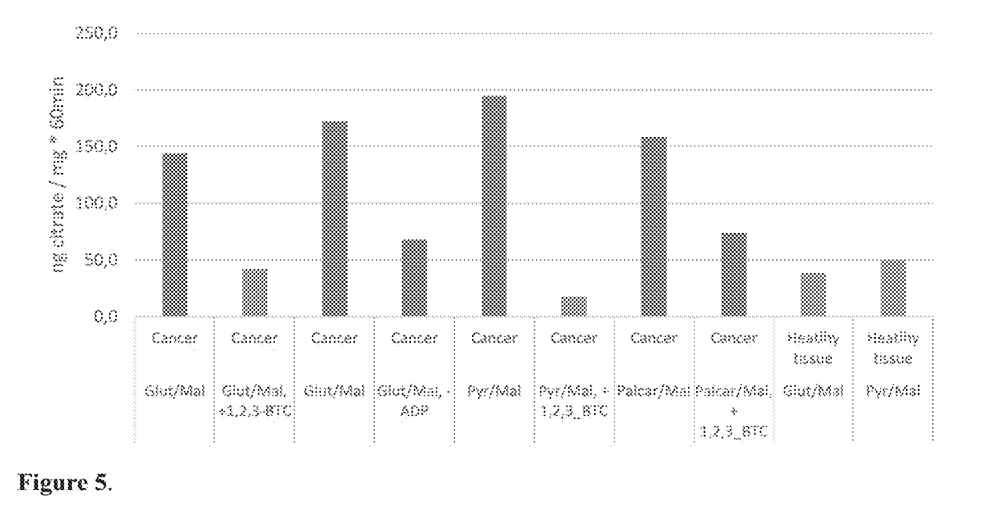
FIG. 5. Experiment results from permeabilized fibers derived from human breast cancer clinical sample. Citrate efflux from the permeabilized human breast cancer and healthy tissue fibers measured as ng citrate/mg weight*hour.

As a result (see FIG. 5), it can be concluded that citrate present in the reaction medium is coming predominantly from mitochondria (as 1,2,3-BTC blocked the citrate accumulation in the reaction medium; or it is coming from other organelles with citrate transporters susceptible to 1,2,3-BTC inhibition). In addition, citrate efflux from cancerous permeabilized tissue is significantly higher than that from the healthy tissue (the latter did not exceed detection limit) and the process is ADP-dependent (as citrate efflux is lower without ADP).

Two separate tests were done on the same tumor based on protocol nr 1 (glutamate and malate as substrates). Respective results were 144.1 vs 172.1 (mean 158.1 ng citrate/mg sample weight×hour), indicating to possible tumor heterogeneity.

Figure 6:
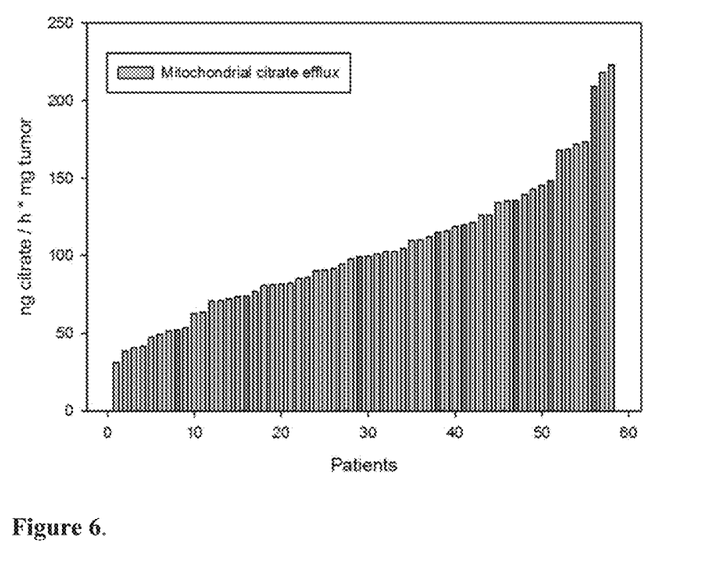
FIG. 6. Results spectrum for human breast cancer patients.

Example 4. Comparison of Results for Mitochondrial Citrate and Glutamate Efflux from Permeabilized Clinical Samples In FIG. 6, citrate efflux results from 58 breast cancer patient samples have been drawn. It is evident from the graph that breast cancer patients' diseases form a spectrum with metabolically less active tumors locating to the left on the graph and more active (e.g. aggressive) tumors locating to the right on the graph.

Figure 7:
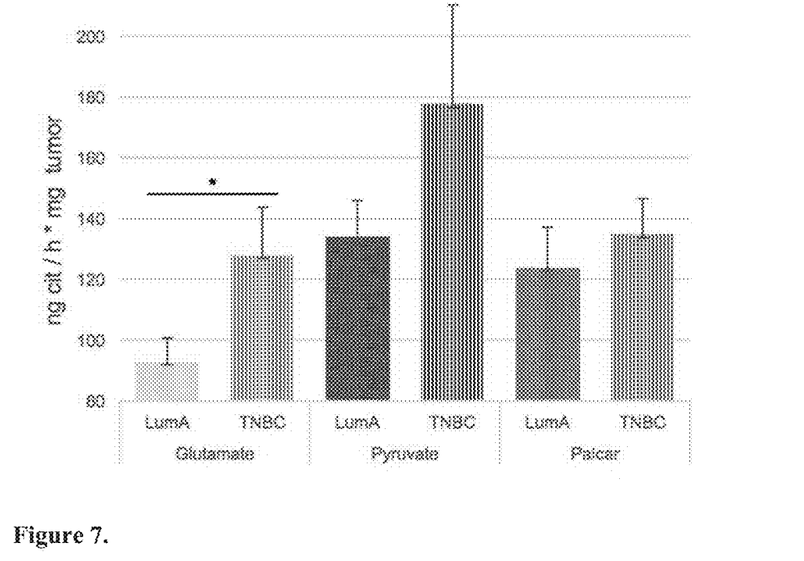
FIG. 7. Mitochondrial citrate efflux in luminal-A and triple-negative breast cancer subtypes.

On FIG. 7, citrate efflux rates only for least aggressive luminal-A and most aggressive triple-negative (TNBC) subtypes are compared. TNBC directs more pyruvate to citrate efflux than luminal-A type tumors, but also uses significantly more glutamate (a product of glutaminalysis) for mitochondrial citrate efflux, possibly indicating to elevated uptake and dependence on its precursor, glutamine. Use of acylcarnitines for the citrate efflux is close to equal.

Figure 8:
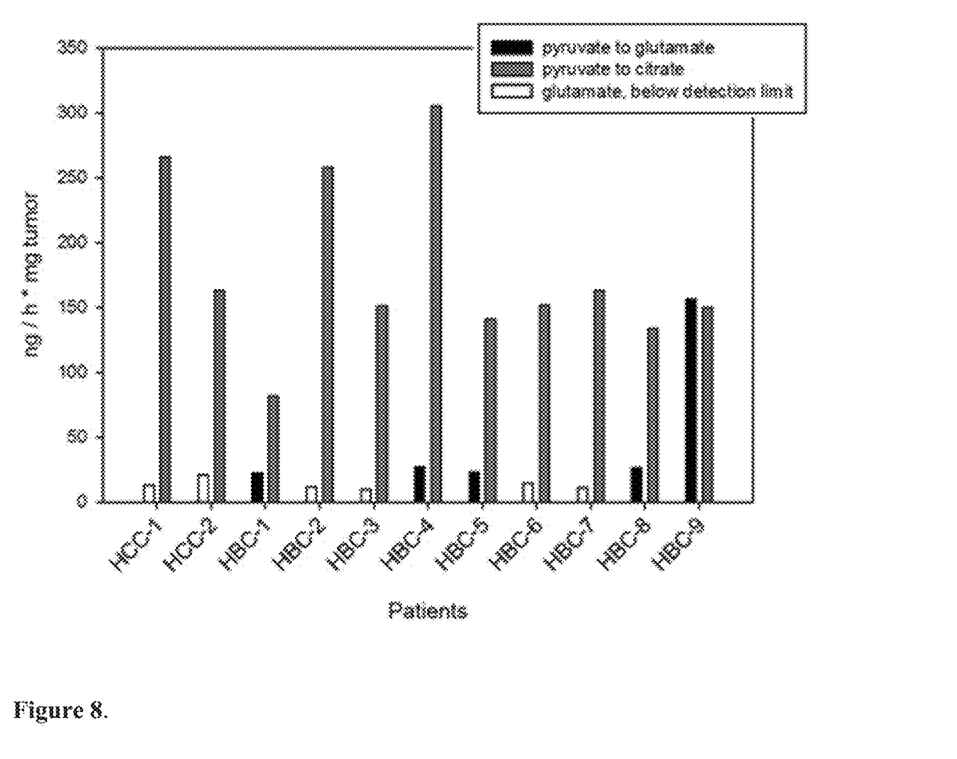
FIG. 8. Citrate and glutamate efflux from permeabilized human breast cancer (HBC) and colorectal cancer (HCC) samples.

In FIG. 8, citrate results from a selection of the patients have been co-displayed with glutamate efflux results from the same tumor samples. HCC stands for colorectal and HBC for patients with breast cancer. Glutamate results for patient HBC-9 has been gained using permeabilization process in the reaction medium during the induction phase without subsequent washing of the sample (i.e. without removing the cytosolic fraction from the reaction medium).

Figure 9:
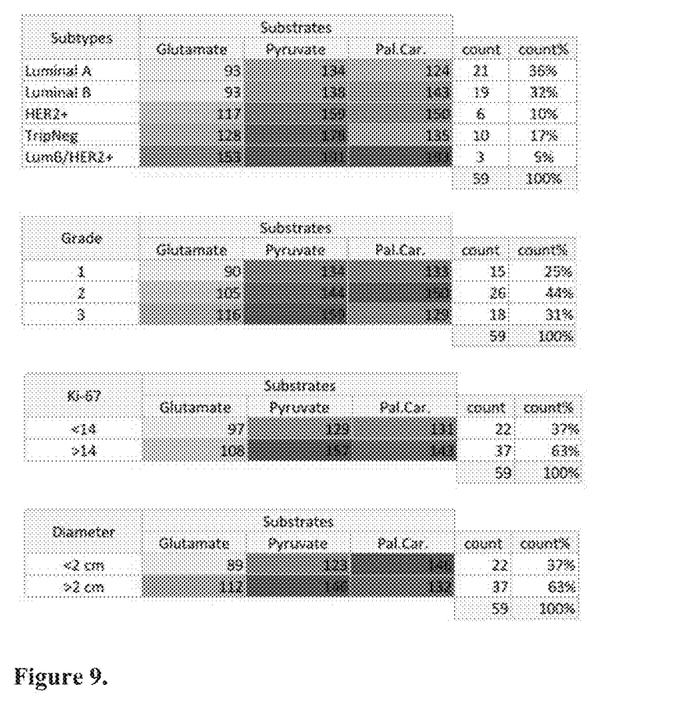
FIG. 9. Mitochondrial citrate efflux vs. standard pathological markers.
Figure 10:
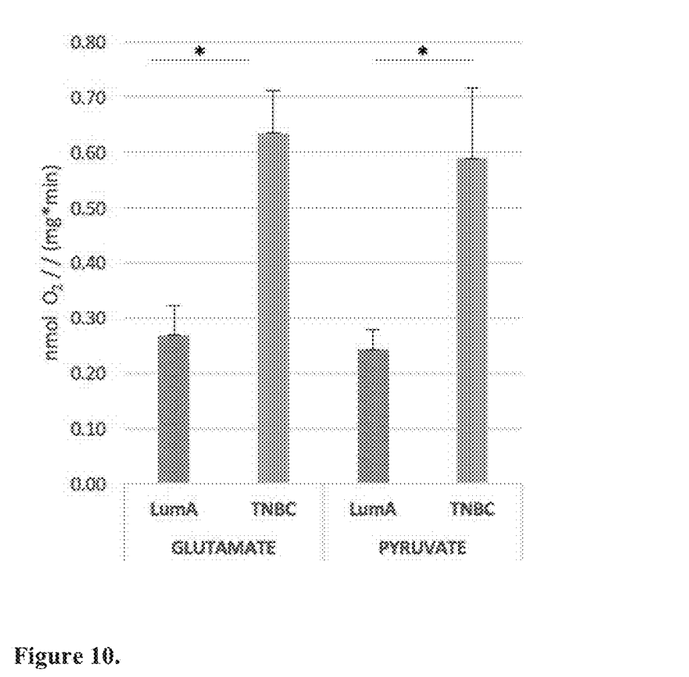
FIG. 10. Difference in respiration rates for luminal-A and TNBC breast cancer subtypes.

On FIG. 9, further outcome is drawn when mitochondrial citrate efflux rates are compared to standard clinical pathology markers. It becomes evident that increasing aggressiveness of the disease, as described by standard pathology markers, is accompanied by elevated metabolic activity as shown by increasing mitochondrial citrate efflux rates based on pyruvate or glutamate as substrates. Increased metabolic activity along the aggressiveness axis is further described by significantly different respiration rates between the least aggressive luminal-A and the most aggressive TNBC subtypes as indicated on FIG. 10 (glutamate or pyruvate as substrates). In conclusion, the more aggressive a tumor is, the more it needs its mitochondria to have elevated respiratory capacity together with elevated capacity to replenish different metabolite pools and these differences can be basis for predicting response to drugs used against the measured pathways.

REFERENCES

US20160320316
US20020127619
Petrarulo et al., 1995, Citrate in Urine Determined With a New Citrate Lyase Method, Clin Chem 41(10):1518-1521.

The invention claimed is:

1. A method of quantifying intracellular metabolite effluxes in permeabilized cancer cells for selecting cancer patients responsive for a cancer treatment, the method comprising the steps of:
    a) providing a sample of cancer cells taken from a patient;
    b) permeabilizing said cancer cells;
    c) incubating said permeabilized cancer cells in a reaction medium for a period of time allowing biological activity of intracellular organelles and accumulation of one or more metabolites produced by said activity into the reaction medium in the presence of two or more substrates relating to a metabolite efflux or effluxes of interest, wherein the two or more substrates comprise at least glutamine and pyruvate;
    d) determining a quantity of the one or more metabolites relating to said metabolite efflux or effluxes of interest accumulated in the reaction medium during step c); and
    e) comparing the quantity of one or more metabolites determined in step d) to equivalent measurements performed on control samples of the same tissue type as the cancer cells; and
    f) if a difference between the quantity of one or more metabolites in step d) and those of the control samples indicate elevated metabolic activity of the cancer cells, contacting the cancer cells with a drug affecting a metabolic pathway or pathways relating to said metabolite efflux or effluxes of interest to determine a treatment response of the cancer cells to the drug, wherein the drug comprises a glutaminase (GLS) inhibitor.

2. The method according to claim 1, wherein the cells are permeabilized in step b) by electro-permeabilization or by contacting the cells with a permeabilization agent.

3. The method according to claim 2, wherein said permeabilization agent is selected from the group consisting of: saponin and digitonin.

4. The method according to claim 1, wherein the one or more metabolites determined in step d) are selected from the group consisting of: pyruvate, glutamine, glutamate, citrate, iso-citrate, alpha-ketoglutarate, aspartate, alanine, glycine, succinate, fumarate, malate, and oxaloacetate.

5. The method according to claim 4, wherein the metabolites determined in step d) are pyruvate and glutamine.

6. The method according to claim 1, wherein the two or more substrates relating to a metabolite efflux or effluxes of interest in step c) further comprise an additional substrate selected from the group consisting of: citrate, iso-citrate, glutamate, alpha-ketoglutarate, succinate, acylcarnitine, ornithine, arginine, formate, proline, and malate.

7. The method according to claim 6, wherein the additional substrate comprises an acylcarnitine.

8. The method according to claim 1, wherein, in a control sample, said substrate relating to a metabolite efflux of interest in step c) is an inhibitor of said metabolite efflux.

9. The method according to claim 1, wherein the one or more metabolites determined in step d) are selected from the group consisting of: folate, ATP, ADP, citrulline, ornithine, δ-aminolevulinic acid, arginine, asparagine, cysteine, histidine, isoleucine, leucine, lysine, methionine, proline, serine, threonine, tryptophan, phenylalanine, tyrosine, valine, $H_2O_2$, carnitine, phosphoenolpyruvate, formate, urea, and 2-hydroxy-glutarate.

10. The method according to claim 1, wherein said control samples in step e) are healthy tissue samples taken from said patient.

11. The method according to claim 1, wherein said period of time in step c) is 0.1-180 minutes.

12. The method according to claim 1, wherein said cancer cells are from breast cancer.

13. The method according to claim 1, wherein the treatment response of the cancer cells to a drug affecting a metabolic pathway is assessed in step e) based on a metabolic dependency of the cancer cells shown by the results obtained in step d).

14. The method according to claim 13, wherein said cancer cells are dependent on glutamine.

15. The method according to claim 1, wherein an aggressiveness of the cancer cells is assessed in step e) based on the metabolic activity of the cancer cells shown by the results obtained in step d) so that metabolically more active cells correspond to an aggressive cancer, and metabolically less active cells correspond to a less aggressive cancer.

16. A method for selectively treating cancer patients comprising:
    a) providing a sample of cancer cells taken from a patient;
    b) permeabilizing said cancer cells;
    c) incubating said permeabilized cancer cells in a reaction medium for a period of time allowing biological activity of intracellular organelles and accumulation of one or more metabolites produced by said activity into the reaction medium in the presence of two or more substrates relating to a metabolite efflux or effluxes of interest, wherein the two or more substrates comprise at least glutamine and pyruvate;
    d) determining a quantity of the one or more metabolites relating to said metabolite efflux or effluxes of interest accumulated in the reaction medium during step c); and
    e) comparing the quantity of one or more metabolites determined in step d) to equivalent measurements performed on control samples of the same tissue type as the cancer cells; and
    f) if a difference between the quantity of one or more metabolites in step (d) and those of the control samples indicate elevated metabolic activity of the cancer cells, administering to the patient an amount of a drug affecting a metabolic pathway or pathways relating to said metabolite efflux or effluxes of interest, wherein the drug comprises a glutaminase (GLS) inhibitor.

* * * * *